United States Patent [19]

Smith

[11] Patent Number: 5,026,356
[45] Date of Patent: Jun. 25, 1991

[54] SAFETY DEVICE FOR NEEDLES OF HYPODERMIC SYRINGES

[76] Inventor: Daniel E. Smith, 6377 Post Town Rd., Dayton, Ohio 45426

[21] Appl. No.: 598,980

[22] Filed: Oct. 17, 1990

[51] Int. Cl.$^5$ ............................................. A61M 5/32
[52] U.S. Cl. .................................... 604/192; 604/198; 604/263
[58] Field of Search ................ 604/192, 187, 263, 198

[56] References Cited

U.S. PATENT DOCUMENTS

| | | |
|---|---|---|
| 1,921,034 | 8/1938 | LaMarche . |
| 2,854,976 | 10/1958 | Heydrich . |
| 3,658,061 | 4/1972 | Hall . |
| 4,425,120 | 1/1984 | Sampson et al. ..................... 604/198 |
| 4,573,976 | 3/1986 | Sampson et al. ..................... 604/198 |
| 4,655,751 | 4/1987 | Harbaugh ............................ 604/198 |
| 4,747,836 | 5/1988 | Luther ................................. 604/198 |
| 4,795,443 | 1/1989 | Permelter et al. .................. 604/198 |
| 4,915,696 | 4/1990 | Feimer ................................ 604/192 |

Primary Examiner—John D. Yasko
Attorney, Agent, or Firm—Ralph L. Marzocco

[57] ABSTRACT

Hypodermic syringes with accompanying hypodermic syringe needles may readily utilize the disclosed safety device to achieve less operator risk of needle stick injury and less risk of body fluid contamination. In the preferred embodiment the safety device, which can be releasably affixed to the barrel of a hypodermic syringe having an attached hypodermic syringe needle, has a channel-like member that houses a forwardly movable, generally L-shaped member and a rocker spring. After injecting substances into or withdrawing body fluids from a human being or an animal, the L-shaped member is pushed forwardly somewhat beyond the tip of the hypodermic syringe needle. The downwardly action of the rocker spring cooperating with the design features of the L-shaped member causes the L-shaped member to move downwardly past the tip of the hypodermic syringe needle and then rearwardly so that the tip of the hypodermic syringe needle becomes embedded into the L-shaped member.

22 Claims, 3 Drawing Sheets

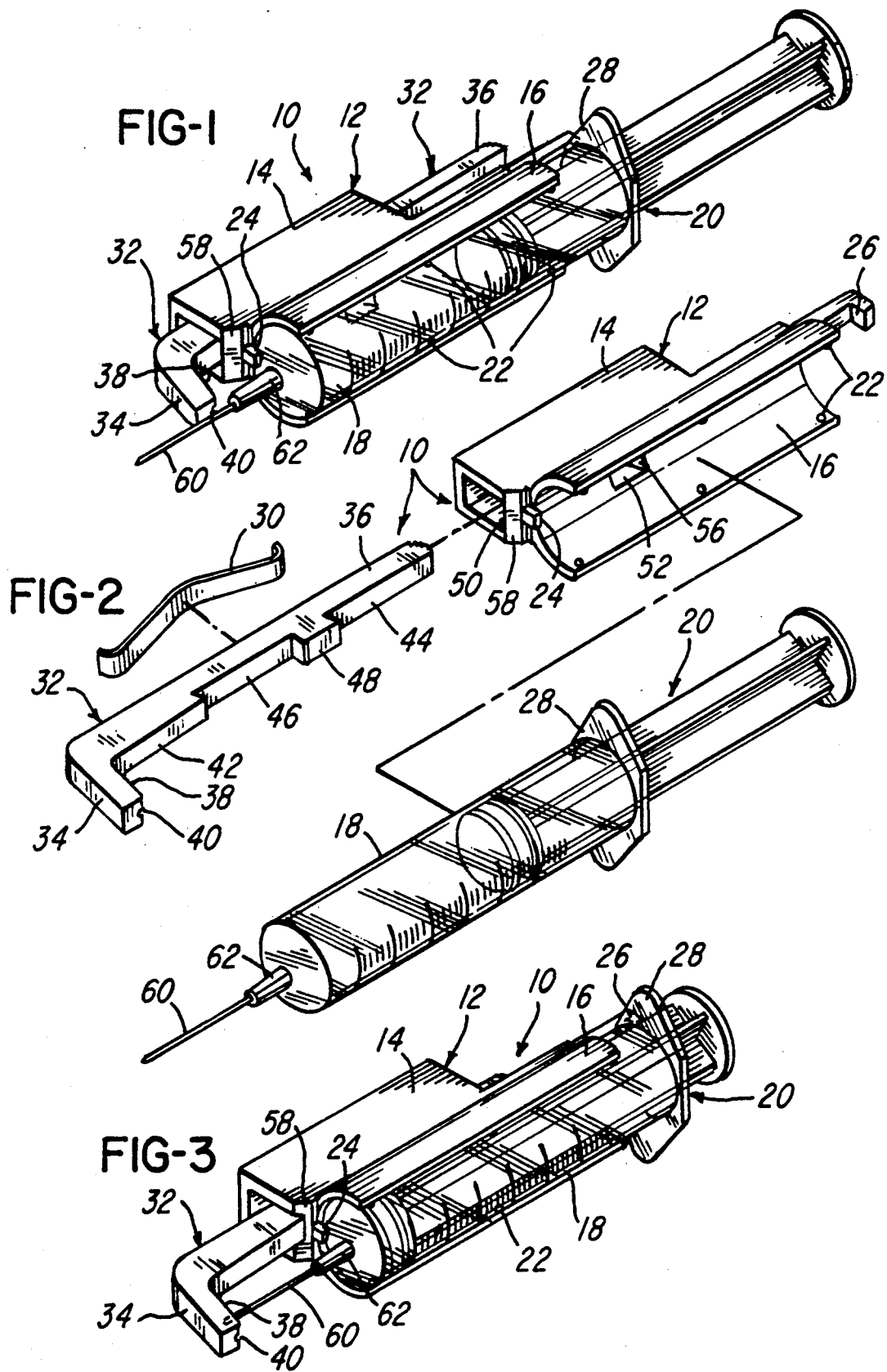

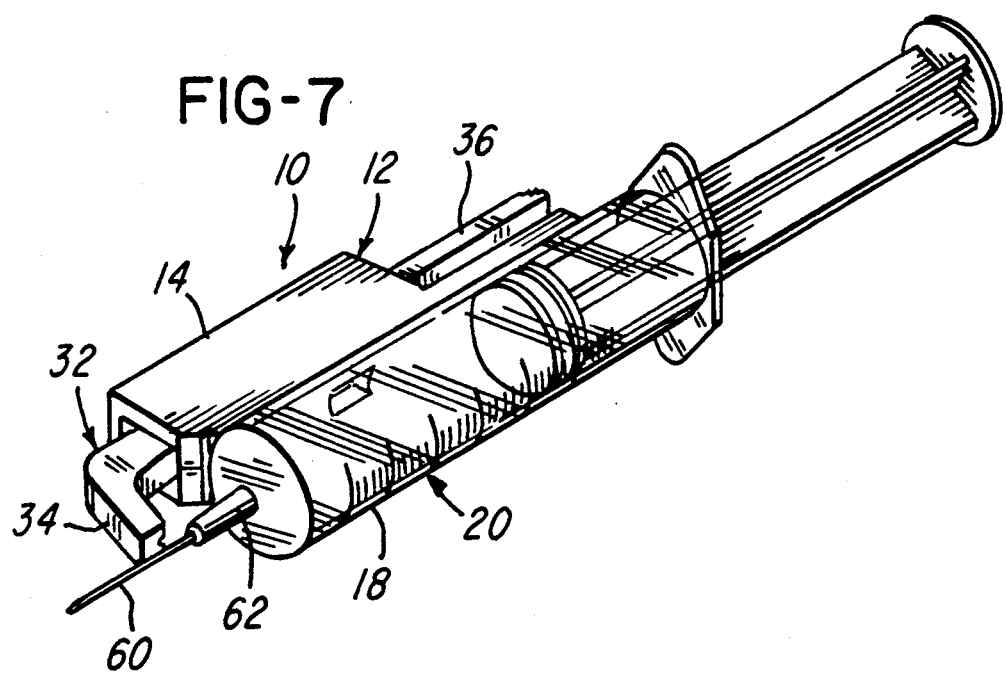

SAFETY DEVICE FOR NEEDLES OF HYPODERMIC SYRINGES

BACKGROUND OF THE INVENTION

1. Field of the Invention

The present invention generally relates to hypodermic syringes and accompanying needles for injecting substances into—or withdrawing fluids from—a human being or an animal. More particularly, the invention relates to a safety device for embedding the tip of a syringe needle into embeddable matter in order to prevent accidental needle stick injury.

2. Description of the Prior Art

More than ever before considerable operator risk is associated with the use of hypodermic syringes and accompanying needles for injecting substances into donees or withdrawing fluids from donors. For when a syringe and needle are exposed to a virulent contagion, life threatening disease may be transmitted from the donor or donee to the operator of the syringe. In order to minimize accidental transmission of such contagion, current medical practice prescribes that hypodermic syringes and needles be discarded after one-time use. Additionally, prior to discard, current medical practice prescribes that the sharp end of needles be embedded in an embeddable substance to prevent accidental needle stick injury. This is usually accomplished by the operator pushing the needle of the hypodermic syringe held in one hand into a cork, rubber stopper, or the like held in the other hand. Once the tip of the needle is embedded, the operator and all others are protected from accidental needle stick. However, in any attempt to embed the tip of a needle into embeddable matter, operator error may cause a needle to puncture the skin of the operator.

Alternative devices for embedding, sealing, guarding, protecting, shielding, or enclosing needles of hypodermic syringes, whose purpose is to prevent needle stick injury and contamination of samples of body fluids, have been devised. Representative of the prior art are the hypodermic syringe arrangements disclosed in U.S. Pat. Nos. 4,795,443 (Permenter et al), 4,747,836 (Luther), 4,655,751 (Harbaugh), 4,573,976 (Sampson et al), 4,425,120 (Sampson et al), 3,658,061 (Hall), 2,854,976 (Heydrich), and 1,921,034 (Marche).

U.S. Pat. No. 4,795,443 discloses a needle of hypodermic syringe sealing device with a cap that can be slid forwardly past the tip of the needle and then rearwardly so that the end of the needle becomes sealed in the cap.

U.S. Pat. Nos. 4,747,836 and 3,658,061 disclose a needle of hypodermic syringe guarding devices with slotted cylinders which, before use, are rotated away from the needle and which, after use, are rotated back to once again enclose the needle.

U.S. Pat. Nos. 4,665,751 and 2,845,976 respectively disclose a needle of hypodermic syringe protecting devices with a cylindrical shell slidable between a needle exposing position and a needle covering position or a cylindrical shell removable for a needle exposing position and engageable for a needle covering position.

U.S. Pat. Nos. 4,573,976 and 4,425,120 disclose a needle of hypodermic syringe shielding devices with a guard movable between an extended needle-shielding position and a retracted needle-nonshielding position.

U.S. Pat. No. 1,921,034 discloses an enclosing device for a hypodermic syringe and needle sealable within an enclosure in a carrying position and advanceable to an exposing position where the needle projects beyond the end of the enclosure.

While many of the structural arrangements of improved hypodermic syringes for preventing air contamination of samples of body fluids and accidental needle stick injury appear to function reasonably well and generally achieve their objectives, most seem to embody shortcomings which make them less than optimum design. For instance, many do not provide positive means for embedding the tip of the needle into embeddable matter or positive means for retaining the embedded needle in embeddable matter. Consequently, a need still exists for a different approach in the design of an improved hypodermic syringe. It is to the provision of such that the present invention is primarily directed.

SUMMARY OF THE INVENTION

Hypodermic syringes with accompanying needles may readily utilize the safety device of the present invention to inject substances into or withdraw body fluids from a human being or animal with less operator risk of needle stick injury and less risk of body fluid contamination than heretofore possible. Such safety device is easily adapted for use with hypodermic syringes of various shapes and sizes.

In accordance with the teachings of the present invention, the safety device is securely affixed to the barrel of a hypodermic syringe having a needle attached at one end of the syringe. The safety device has a channel which houses a forwardly movable, generally L-shaped member. After the injection of a fluid substance into a donee, or in the alternative, after the withdrawal of body fluids from a donor, the operator pushes the L-shaped member forwardly somewhat beyond the tip of the needle. The design features of the L-shaped member cooperating with a rocker spring causes the member to move downwardly past the tip of the needle and then rearwardly causing the tip of the needle to become embedded into the L-shaped member.

After a substance has been injected into a donee, the hypodermic syringe and the safety device with the embedded needle may be disposed, or alternatively, the safety device with the embedded needle may be disconnected from the hypodermic syringe and the safety device with the embedded needle may be disposed while the hypodermic syringe may be reused upon sterilization. After a body fluid has been withdrawn from a donor, the safety device with the embedded needle may be disconnected from the hypodermic syringe and the contents of the hypodermic syringe may be discharged into a sterile receptacle. The hypodermic syringe and safety device with the embedded needle may be disposed, or alternatively, the safety device with the embedded needle may be disposed while the hypodermic syringe may be reused upon sterilization.

These and other advantages and attainments of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

For a further understanding of the nature and object of the invention, reference should be had to the detailed description of the exemplary embodiments taken in connection with the appended drawings in which:

FIG. 1 is a perspective view of the safety device of this invention securely affixed to the barrel of a hypodermic syringe having a needle attached at one end of the syringe.

FIG. 2 is an exploded perspective view of the safety device of this invention and a hypodermic syringe having a needle attached at one end of the syringe FIG. 3 is a perspective view of the safety device of this invention securely affixed to the barrel of a hypodermic syringe having a needle attached at one end of the syringe. The tip of the needle is embedded into an L-shaped member of the safety device.

FIG. 7 is a perspective view of the safety device of this invention integral to the barrel of a hypodermic syringe having a needle attached at one end of the syringe.

DETAILED DESCRIPTION OF THE INVENTION

Figure 4:
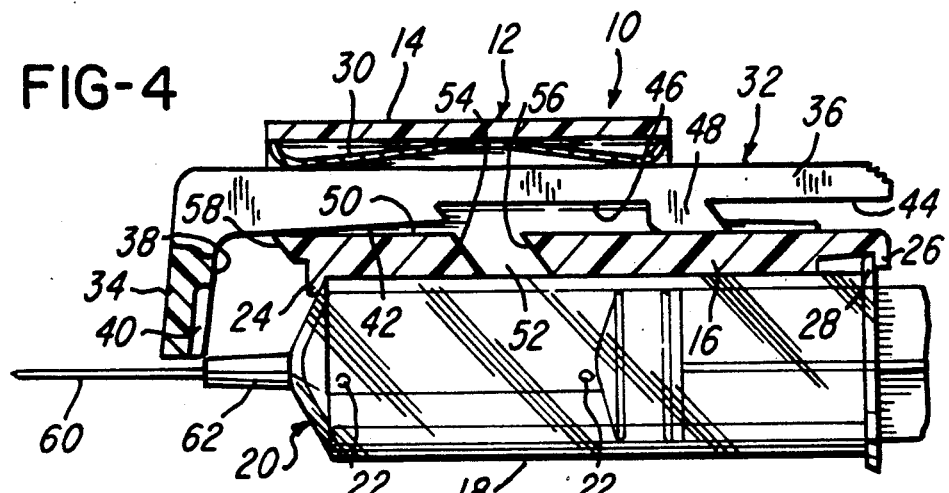
FIG. 4 is a side cross sectional view of the safety device of this invention securely affixed to the barrel of a hypodermic syringe having a needle attached at one end of the syringe. The shorter arm of an L-shaped member of the safety device is positioned somewhat above and toward the rearward portion of the needle.

In the following description, like reference characters designate like or corresponding parts throughout the several views of the drawings. Also in the following description, it is to be understood that such terms as "forward", "rearward", "left", "right", "upwardly", "downwardly", and the like, are words of convenience and are not to be construed as limiting terms.

Referring now to the drawings, and particularly to FIGS. 1-2, there is illustrated a safety device for needles of hypodermic syringes, generally designated by the numeral 10 and constituting the preferred embodiment of the present invention, being shown assembled in FIG. 1 and disassembled in FIG. 2. In such embodiment device 10 combines a protective and safety component with a hypodermic syringe component. A modified embodiment of the present invention is illustrated in FIG. 7. In such embodiment the protective and safety component and the hypodermic syringe component are an integral unit.

The protective and safety component of device 10 is an elongated structure 12 which comprises a four sided, open ended, channel-like member 14 and an elongated, longitudinally slotted, sleeve member 16 that snugly and circumferentially encases an outer wall 18 of a hypodermic syringe 20. Sleeve member 16 which is formed from a flexible substance has a plurality of bosses 22 proximate the longitudinal edges of its inner wall for firmly affixing elongated structure 12 to outer wall 18 of hypodermic syringe 20.

Channel-like member 14 is partially integral with sleeve member 16 and is located atop and equidistant from the longitudinal edges of sleeve member 16. Extending downwardly at the forward portion of channel-like member 14 is a forward tab stop 24 for preventing forward movement of hypodermic syringe 20 when firmly encased within sleeve member 16. Extending downwardly at the rearward portion of channel-like member 14 is a rearward tab stop 26 for preventing rearward movement of hypodermic syringe 20 when firmly encased within sleeve member 16. When forward tab stop 24 contacts the closed end of hypodermic syringe 20, rearward tab stop 26 snugly fits over an opening lip 28 of the barrel of hypodermic syringe 20. As can be readily appreciated, the combination of forward tab stop 24 and rearward tab stop 26 cooperating with sleeve member 16 with its numerous bosses 22 secures safety device 10 to hypodermic syringe 20. Yet, when needed, because of the flexible nature of the substance from which sleeve member 16 is fabricated, hypodermic syringe is releasable from safety device 10.

As mentioned above, channel-like member 14 is integral with a portion of sleeve member 16. Incorporated within channel-like member 14 is a rocker spring 30 and a slidable member 32. Rocker spring 30 which is fabricated from a flexible substance defines an elongated, curved plate whose ends are oppositely curved. Slidable member 32 is generally L-shaped having a shorter arm 34 defining an angle with a longer arm 36 that is somewhat greater than a normal angle. An inner wall 38 of shorter arm 34 defines an elongated recess 40 which is approximately one-half the height of shorter arm inner wall 38 and which is equidistant from the outer edges of shorter arm inner wall 38. The outer wall surface of both shorter arm 34 and longer arm 36 of L-shaped member 32 are planar.

Figure 5:
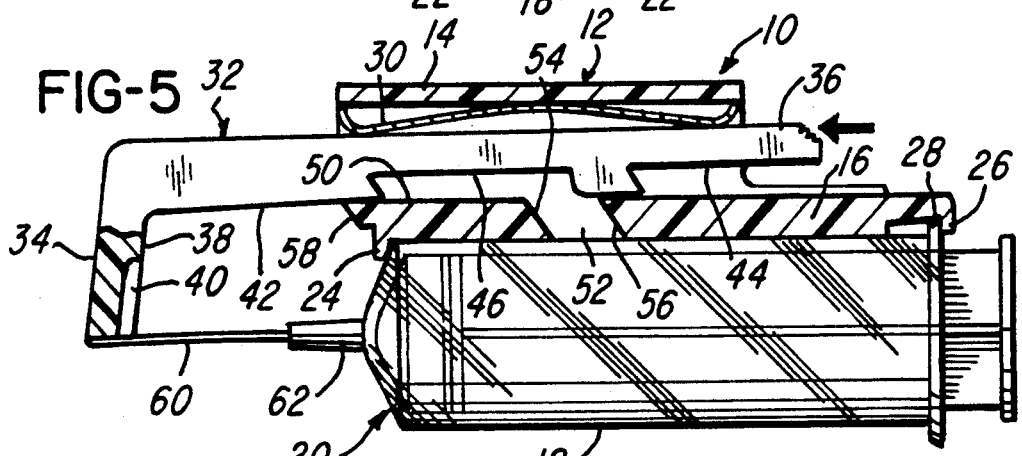
FIG. 5 is a side cross sectional view of the safety device of this invention affixed to the barrel of a hypodermic syringe having a needle attached at one end of the syringe. The shorter arm of an L-shaped member of the safety device is positioned in contact with and toward the forward portion of the needle.
Figure 6:
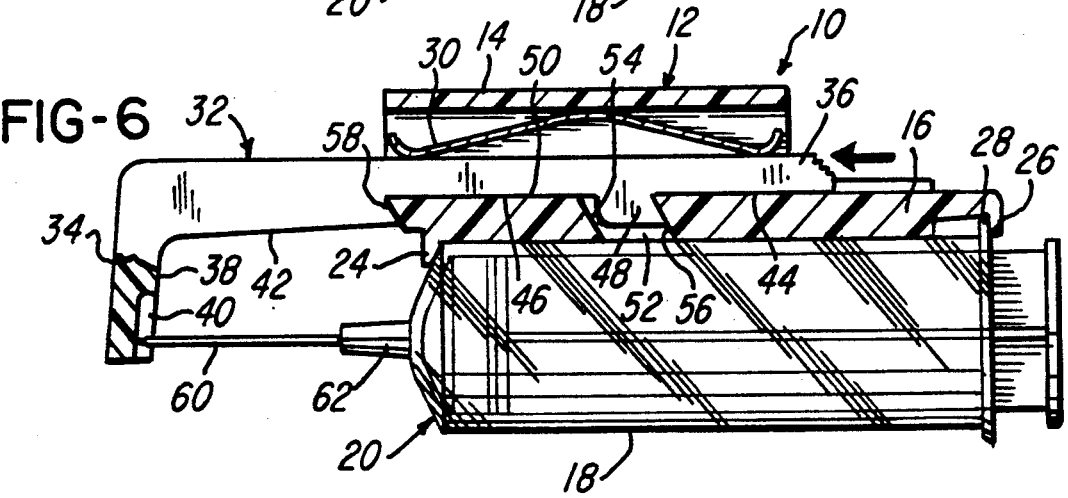
FIG. 6 is a side cross sectional view of the safety device of this invention securely affixed to the barrel of a hypodermic syringe having a needle attached at one end of the syringe. The tip of the needle is embedded into the shorter arm of an L-shaped member of the safety device.

Referring again to the drawings showing slidable L-shaped member 32 and particularly to FIGS. 4-6, it can be readily seen that an inner bottom wall 42 of longer arm 36 is downwardly inclined from the rearward end of longer arm 36 to the forward point of intersection with shorter arm 34. However, inner bottom wall 42 is not entirely planar but rather a wall with two consecutively spaced slots. At that portion of inner bottom wall 42 more distant from shorter arm 34 is a first slot 44 while at that portion of inner bottom wall 42 less distant from shorter arm 34 is a second slot 46. Perforce first slot 44 and second slot 46 are separated from one another by an intervening, generally trapezoidal-shaped portion 48 of L-shaped member 32. The forward walls of slots 44 and 46 are parallel to each other and define with respect to inner bottom wall 42 an angle that is greater than a normal angle resulting in an inclined plane directed away from shorter arm 34. The rear wall of second slot 46 defines a normal angle with respect to inner bottom wall 42, while first slot 44 has no rear wall but is open-ended.

A bottom wall 50 of channel-like member 14 has an opening 52 therethrough which defines a forward opening wall 54 and a rearward opening wall 56. Forward opening wall 54 and rearward opening wall 56 define planes which are parallel to one another and are inclined at such an angle so that they are parallel to the forward walls of first slot 44 and second slot 46. Additionally, the forward portion of bottom wall 50 is designed to define an end wall 58 which is inclined at such an angle so that it is also parallel to the forward walls of first slot 44 and second slot 46.

Whenever an injection of a substance or a withdrawal of a fluid is to be made, a sterile hypodermic syringe needle 60 and safety device 10 are affixed to hypodermic syringe 20. This is accomplished by manually pressing syringe needle 60 onto a conventional mounting member 62 of hypodermic syringe 20 and positionally affixing safety device 10 onto outer wall 18. When properly positioned, the combination of tab stops 24,26 cooperating with sleeve member 16 with its numerous bosses 22 secures safety device 10 to hypodermic syringe 20. At this time, as shown in FIG. 4, slidable L-shaped member 32 is in a fully retracted position with the bottom portion of shorter arm 34 of L-shaped member 32 being positioned somewhat above syringe needle 60.

After an injection of a substance or withdrawal of a fluid has been made, an operator (not shown) forwardly pushes slidable L-shaped member 32 with one hand while holding the combination of safety device 10 and hypodermic syringe 20 in the other hand. (Smaller versions of the combination of safety device 10 and hypodermic syringe 20 can be operated with but one hand and thus, immeasurably reduce the chance of accidental needle stick injury.) As shown in FIG. 5, L-shaped member 32 in its forwardly travel reaches a position where the bottom portion of shorter arm 34 contacts hypodermic syringe needle 60 caused by the downwardly inclined disposition of inner bottom wall 42 of longer arm 36. (The slope of inner bottom wall 42 of longer arm 36 with respect to the longitudinal axis of hypodermic syringe 20 is equal to an angle that causes shorter arm 34 in the fully retracted position to be somewhat above hypodermic syringe needle 60 but when forward near the tip of hypodermic syringe needle 60 to be in contact with hypodermic syringe needle 60.)

As shown in FIG. 6, with additional forward travel of L-shaped member 32, shorter arm 34 clears the tip of hypodermic syringe needle 60, forward wall of second slot 46 clears end wall 58 of bottom wall 50, and forward wall of first slot 44 clears rearward opening wall 56 of bottom wall opening 52, causing shorter arm 34 and intervening trapezoidal-shaped portion 48 of L-shaped member 32 to be forced downwardly by the bias action of rocker spring 30, and in turn causing the tip of hypodermic syringe needle 60 to be enveloped by shorter arm elongated recess 40 and intervening trapezoidal-shaped portion 48 to be enveloped in the chamber formed by bottom wall opening 52. When the forward wall of intervening trapezoidal-shaped portion 48 contacts the inclined, forward opening wall 54, the continuing bias action of rocker spring 30 causes slidable L-shaped member 32 to travel somewhat backwardly until intervening trapezoidal-shaped portion 48 fits snugly in the chamber of bottom wall opening 52. Simultaneously, because of the backwardly travel of L-shaped member 32, the tip of hypodermic syringe needle 60 in elongated recess 40 is embedded into shorter arm 34. Safety device 10, hypodermic syringe 20, and hypodermic syringe needle 60 can then be safely handled with negligible chance of accidental needle stick injury. And they are reusable. In summary, when slidable L-shaped member 32 is pushed forwardly, the action of rocker spring 30 upon the structural configuration of slidable L-shaped member 32 cooperating with the structural configuration of channel-like member 14 causes hypodermic syringe needle 60 to become embedded in the shorter arm 34 of slidable member 32.

However, if a safe, disposable hypodermic syringe/needle unit is preferred, it is manifestly evident that the protective and safety component can be integrally combined with the hypodermic syringe component. As shown in FIG. 7, elongated, longitudinally slotted, sleeve member 16 of protective and safety component of device 10 no longer snugly encases outer wall 18 of hypodermic syringe 20, it has been eliminated as are tab stops 24,26. Integral with outer wall 18 of hypodermic syringe 20 is channel-like member 14 forming a unitized design. Slidable L-shaped member 32 and rocker spring 30 (not shown) are designed and function as above disclosed.

As can be seen in the illustrations and as described in the specification, the present invention will considerably reduce operator risk associated with hypodermic syringes and accompanying needles used to inject substances into donees or withdraw fluids from donors. Additionally, the combination of a device of the present invention and a hypodermic syringe and a hypodermic syringe needle are reusable.

It is thought that the present invention and many of its attendant advantages will be understood from the foregoing description and it will be apparent that various changes may be made in the form, construction, and arrangement of the parts thereof without departing from the spirit and scope of the invention or sacrificing all of its material advantages, the form hereinabove described being merely preferred or exemplary embodiments thereof.

I claim as my invention:

1. A safety device for a hypodermic syringe and an accompanying hypodermic syringe needle comprising:
    an elongated structure having a channel-like member with an opening in the floor of the channel-like member and having a flexible, longitudinally slotted sleeve member for releasable attachment of the structure to a hypodermic syringe;
    securement means for preventing forward and rearward movement of the structure with respect to the hypodermic syringe;
    a L-shaped member having an elongated recess in the backside of its shorter arm and having a plurality of slots in the bottomside of its longer arm, the L-shaped member being forwardly and downwardly slidable in the channel-like member;
    a rocker spring housed in the channel-like member for downwardly urging the slidable L-shaped member; and
    structural means for embedding a hypodermic syringe needle of the hypodermic syringe into the recess of the back wall of the shorter arm of the slidable L-shaped member in response to the downwardly urging of the rocker spring.

2. The device according to claim 1, wherein a portion of the channel-like member is integral with a portion of the slotted sleeve member and is located atop and equidistant from the longitudinal edges of the sleeve member.

3. The device according to claim 1, wherein the forward portion of the floor of channel-like member is downwardly and rearwardly inclined.

4. The device according to claim 1, wherein the longitudinally slotted sleeve member has a plurality of bosses proximate to the longitudinal edges of its inner wall.

5. The device according to claim 1, wherein the longitudinally slotted sleeve member snugly and circumferentially encases the outer wall of the hypodermic syringe.

6. The device according to claim 1, wherein the securement means for preventing forward and rearward movement of the elongated structure with respect to the hypodermic syringe comprises a tab stop extending downwardly from the bottomward and forward portion of the elongated structure and a tab stop extending downwardly from the bottomward and rearward portion of the elongated structure.

7. The device according to claim 1, wherein the longer arm of the L-shaped member from its rearward end to its forward end is downwardly inclined.

8. The device according to claim 1, wherein the shorter arm of the L-shaped member with respect to the longer arm of L-shaped member defines a somewhat greater than a normal angle.

9. The device according to claim 1, wherein the elongated recess of the L-shaped member is equidistant from the outer edges of the back wall of the shorter arm.

10. The device according to claim 1, wherein the forward walls of the slots of the L-shaped member are parallel to each other and each define an inclined plane directed away from the inclined plane of the back wall of the shorter arm of the L-shaped member.

11. The device according to claim 1, wherein the rearward wall of the more forward slot of the L-shaped member defines a normal angle with respect to the bottom wall of the longer arm of the L-shaped member.

12. The device according to claim 1, wherein the rocker spring is fabricated from a flexible substance that defines an elongated, curved plate whose ends are oppositely curved.

13. The device according to claim 1, wherein the opening in the floor of the channel-like member comprises a forward wall and a rearward wall which are parallel to each other, to the forward walls of the slots of the L-shaped member, and to the forward portion of the floor of the channel-like member.

14. The device according to claim 1, wherein the structural means comprises a trapezoidal-shaped portion intervening between the slots of the L-shaped member.

15. A safety device in combination with a hypodermic syringe and an accompanying hypodermic syringe needle comprising:
an elongated structure having a channel-like member with an opening in the floor of the channel-like member and having a flexible, longitudinally slotted sleeve member releasably attached to a hypodermic syringe;
securement means for preventing forward and rearward movement of the structure with respect to the hypodermic syringe;
a L-shaped member having an elongated recess in the backside of its shorter arm and having a plurality of slots in its longer arm, the L-shaped member being forwardly slidable in the channel-like member;
a rocker spring housed in the channel-like member for downwardly urging the slidable L-shaped member; and
structural means for embedding a hypodermic needle of the hypodermic syringe into the recess of the back wall of the shorter arm of the slidable L-shaped member in response to the downwardly urging of the spring.

16. The device according to claim 15, wherein the forward tab stop contacts the closed end of the hypodermic syringe and the rearward tab stop snugly fits over the opening lip of the barrel of the hypodermic syringe.

17. A safety device integral with a hypodermic syringe and an accompanying hypodermic syringe needle comprising:
an elongated structure having a channel-like member with an opening in the floor of the channel-like member, the structure being integral with a portion of the circumferential wall of a hypodermic syringe;
a L-shaped member having an elongated recess in the backside of its shorter arm and having a plurality of slots in its longer arm, the L-shaped member being forwardly and downwardly slidable in the channel-like member;
a rocker spring housed in the channel-like member for downwardly urging the slidable L-shaped member; and
structural means for embedding a hypodermic syringe needle of the hypodermic syringe into the recess of the back wall of the shorter arm of the slidable L-shaped member in response to the downwardly urging of the spring.

18. The device according to claim 17, wherein the channel-like member and the outer wall of the hypodermic syringe are integrated to form a unitized design.

19. A method for injecting substances into—or alternatively withdrawing fluids from—a human being or an animal using a hypodermic syringe and an accompanying hypodermic syringe needle comprising:
providing an elongated structure having a channel-like member with an opening in the floor of the channel-like member, having a flexible, longitudinally slotted sleeve member, and having securement means for preventing forward and rearward movement;
positionally placing the sleeve member around the barrel of a hypodermic syringe to attach and secure the elongated structure to the hypodermic syringe;
conventionally operating the hypodermic syringe and the accompanying hypodermic syringe needle to inject a substance into—or alternatively to withdraw a fluid from a human being or an animal;
forwardly pushing a L-shaped member disposed in the channel-like member in contact with a downwardly urging spring, the L-shaped member having an elongated recess in the backside of its shorter arm and having a plurality of slots in its longer arm; and
causing the hypodermic needle of the hypodermic syringe to be embedded into the recess of the back wall of the shorter leg of the L-shaped member due to structural means responsive to the downwardly urging of the spring.

20. The method according to claim 19, wherein an operator forwardly pushes the slidable L-shaped member with one hand while holding the combination safety device and hypodermic syringe in the other hand.

21. The method according to claim 20, wherein the downwardly disposed L-shaped member consecutively reaches positions where the bottom portion of the shorter arm of the L-shaped member contacts the hypodermic syringe needle and then clears the tip of the hypodermic syringe needle to be enveloped by the elongated recess of the shorter arm of the L-shaped member.

22. The method according to claim 20, wherein the downwardly urging of the rocker spring causes the intervening trapezoidal-shaped portion of the L-shaped member first to be enveloped in the chamber formed by the opening and then to travel somewhat backwardly causing the tip of the hypodermic syringe needle to be embedded in the elongated recess of the shorter arm of the L-shaped member.

* * * * *